(12) United States Patent
Helmreich et al.

(10) Patent No.: US 8,083,389 B2
(45) Date of Patent: Dec. 27, 2011

(54) MEDICAL EXAMINATION APPARATUS

(75) Inventors: Gerhard Helmreich, Effeltrich (DE); Martin Ramsauer, Pyrbaum (DE); Michael Richenberger, Eckernförde (DE)

(73) Assignee: Siemens Aktiengesellschaft (DE)

( * ) Notice: Subject to any disclaimer, the term of this patent is extended or adjusted under 35 U.S.C. 154(b) by 339 days.

(21) Appl. No.: 12/232,481

(22) Filed: Sep. 15, 2008

(65) Prior Publication Data

US 2009/0080186 A1  Mar. 26, 2009

(30) Foreign Application Priority Data

Sep. 21, 2007 (DE) .......................... 10 2007 045 325

(51) Int. Cl.
*F21V 33/00* (2006.01)
*F21V 7/00* (2006.01)

(52) U.S. Cl. ........ 362/572; 362/602; 362/253; 600/407; 600/424

(58) Field of Classification Search .................. 362/572, 362/231, 253, 234, 602–605, 804, 800; 600/407, 600/424, 418
See application file for complete search history.

(56) References Cited

U.S. PATENT DOCUMENTS

| | | | |
|---|---|---|---|
| 3,892,959 A | | 7/1975 | Pulles |
| 4,613,926 A | | 9/1986 | Heitman et al. |
| 5,134,373 A | | 7/1992 | Tsuruno et al. |
| 5,249,077 A | * | 9/1993 | Laronga et al. ............... 359/385 |
| 5,355,885 A | | 10/1994 | Tsuda et al. |
| 5,835,661 A | | 11/1998 | Tai et al. |
| 6,550,933 B1 | * | 4/2003 | Panz ............................. 362/231 |
| 6,601,985 B1 | * | 8/2003 | Jesurun et al. ................. 362/572 |
| 6,857,772 B2 | * | 2/2005 | Brukilacchio ................. 362/572 |
| 7,567,833 B2 | * | 7/2009 | Moctezuma De La Barrera et al. ............................. 600/424 |
| 7,702,375 B2 | * | 4/2010 | Boninger et al. ............. 600/407 |
| 2004/0131157 A1 | | 7/2004 | Stevanovic et al. |
| 2005/0070779 A1 | * | 3/2005 | Singh B et al. ............... 600/407 |
| 2005/0254256 A1 | | 11/2005 | Gosswein et al. |
| 2006/0052685 A1 | * | 3/2006 | Cho et al. ....................... 600/407 |
| 2007/0053179 A1 | | 3/2007 | Pang et al. |
| 2007/0147087 A1 | | 6/2007 | Parker et al. |

FOREIGN PATENT DOCUMENTS

| | | |
|---|---|---|
| CN | 1518139 A | 8/2004 |
| DE | 44 40 225 A1 | 3/1996 |
| DE | 196 39 923 A1 | 7/1997 |
| DE | 196 29 190 A1 | 1/1998 |
| DE | 100 08 808 A1 | 6/2001 |
| DE | 103 22 140 A1 | 12/2004 |
| DE | 10 2004 024 095 A1 | 12/2005 |

(Continued)

OTHER PUBLICATIONS

European Patent Office Written Opinion dated Nov. 27, 2009 with English translation for corresponding EPO Application No. 08105159.1.

(Continued)

*Primary Examiner* — Bao Q Truong
(74) *Attorney, Agent, or Firm* — Lempia Summerfield Katz LLC (57) ABSTRACT

A medical examination apparatus is provided. The examination apparatus includes an examination area in which an examinee is examined using an imaging device. The examination apparatus includes at least one planar lighting device emitting homogeneous light via its light radiating surface. The lighting device includes at least one light source by which at least part of the examination area and/or of the area peripheral to the examination area can be illuminated.

26 Claims, 4 Drawing Sheets

FOREIGN PATENT DOCUMENTS

| | | |
|---|---|---|
| DE | 10 2005 019 926 A1 | 11/2006 |
| DE | 10 2005 057 371 A1 | 6/2007 |
| GB | 2 383 406 | 6/2003 |
| JP | 63-267344 | 11/1988 |
| JP | 2-98003 | 4/1990 |
| JP | 2-274232 | 11/1990 |
| JP | 2004-89621 | 3/2004 |
| WO | WO 02/084173 A1 | 10/2002 |
| WO | WO 2005/062908 A2 | 7/2005 |

OTHER PUBLICATIONS

German Office Action dated Jul. 2, 2008 with English translation.
German Office Action dated Jul. 2, 2008 for corresponding German Patent Application No. DE 10 2007 045 325.8-35 with English translation.
Chinese Office Action dated Mar. 24, 2011 for corresponding Chinese Patent Application No. 200810154779.7 with English translation.

* cited by examiner

MEDICAL EXAMINATION APPARATUS

The present patent document claims the benefit of 10 2007 045 325.8, filed Sep. 21, 2007, which incorporated by reference.

BACKGROUND

The present embodiments relate to a medical examination apparatus that includes an examination area in which an examinee is examined using an imaging device.

Examination apparatuses are known in different designs and use various imaging devices based on different image capture technologies to create diagnostically useful images of a person to be examined or of a region of a person. The examination apparatuses include, for example, x-ray machines including a radiation source and radiation detector by which x-ray images can be captured. Different types of x-ray apparatus are known, which are sometimes also used for particular diagnostic purposes. For example, a mammography unit used for carrying out breast examinations, X-ray machines with wall-mounted detectors for obtaining images of a standing person, C-arm x-ray machines often guided on supports and ceiling-mounted trolleys. As an alternative to conventional x-ray machines, computed tomography (CT) scanners employ x-ray radiation, but have a usually cylindrical examination area in the form of a patient tunnel into which the patient is introduced on a positioning table. The tunnel is encircled by an x-ray tube so that radiographic images can be acquired from any position. MRI (magnetic resonance imaging) scanners make use of the interaction between an applied magnetic field and electron nuclear spins to produce images. MRI scanners include machines that have an essentially cylindrical patient tunnel into which the patient is introduced lying on a table. However, open systems include two magnets disposed vertically one above the other between which the patient can be introduced from the side.

The examinee is positioned correctly in the examination area in order to ensure that the body region to be examined is correctly positioned in the center of the imaging device. Often actions have to performed on the examinee before the examinee is moved into the examination area or when the examinee is already in the examination area, such as connecting items of equipment or even minor surgical procedures such as taking a biopsy or inserting a catheter. This requires that the person responsible, such as a medical auxiliary or a doctor, has a sufficiently good view of the area in which the examinee is located and in which the person responsible intends to carry out the procedure. As medical examination equipment is often in a windowless or darkened room, which is usually conducive to patient comfort, ceiling-mounted luminaires are regularly used, such as point light sources, which illuminate the room as a whole. Via these luminaires a background light is produced that illuminates the examination area or the periphery of the examination area. However, such illumination is often inadequate, and the problem sometimes arises that the examinee or the person treating the examinee cast shadows.

SUMMARY AND DESCRIPTION

The present embodiments may obviate one or more of the drawbacks or limitations inherent in the related art. For example, in one embodiment, a medical examination apparatus has improved illumination of the examination area and/or the area peripheral area.

In one embodiment, a medical examination apparatus includes at least one planar lighting device emitting homogeneous light via its light radiating surface and includes at least one light source by which at least a part of the examination area and/or the area peripheral thereto can be illuminated.

The examination apparatus has its own built-in lighting device by which the examination area and/or the area peripheral to the examination area can be illuminated. A planar lighting device is used which does not, like normal lighting devices, radiate its light from a single point but has a large light radiating surface, which can be freely sized according to the options available. Depending on the type of examination apparatus, the light radiating surface can be up to 1 $m^2$ or more. The planar lighting device may include a plurality of such planar lighting devices disposed in different positions and having different sizes to be provided on the examination apparatus. The planar lighting devices are positioned such that they can selectively illuminate the examination area and/or the area peripheral thereto which can be optimally and uniformly illuminated, as the lighting device emits homogeneous light over a large light radiating surface.

The large-area, uniform illumination of the relevant areas of the examination apparatus enables the person performing the examination to have an optimum view of the uniformly illuminated area, whether the person is working in the examination area in order, for example, to attach or position an item of equipment (e.g. a coil in the case of an MRI scanner, the compression plate of a mammography unit, etc.), whether it be merely for continuous monitoring during the examination, e.g. to detect any patient movements or the like. The homogeneous radiation of light ensures that not only selective illumination is provided, but also that a large volume is homogeneously illuminated. Altogether homogeneous radiation of light improves working on or with the examination apparatus, and any errors possibly attributable to poor lighting can be avoided.

The planar, homogeneous illumination provides a more pleasant atmosphere than a ceiling-mounted lighting, particularly if the planar lighting device is also in operation during the examination. The planar, homogeneous illumination provides enhanced patient comfort, due also to the effect that the patient is able to orient himself much better in the illuminated examination area or area peripheral because of the optimum illumination of same and can, for example, follow much better any commands of the person carrying out the examination, for example, with respect to positioning, or any movements of part of the examination apparatus.

Any area size of the lighting device or of the lighting device's light radiating surface can be selected insofar as the lighting device can be incorporated on or in the examination apparatus, on or in the examination area or the area peripheral thereto. The lighting device is plate-like and is of flat or curved design depending on where it is mounted. The lighting device delimits at least partly the examination area or area peripheral so that it can illuminate the examination area or its periphery directly. The lighting device is a paneling section which is placed over or fastened to the examination device paneling already provided, or replaces the latter. This provides simple, effective and at the same time visually attractive integrating of the lighting device into already known examination apparatuses.

A planar lighting device has a light-guiding planar element which in turn has a deflecting light coupled in laterally via the at least one light source toward the radiating surface. The light-transparent planar element may be made of glass or preferably plastic, which facilitates shaping. PMMA or PC, for example, can be used as the plastic material. Depending on its total size, the planar element has a thickness ranging from a few millimeters, for example, 5 mm, to a few centimeters, for example, 2 cm, enabling it to be endowed with sufficient intrinsic stiffness even if the planar element is itself very large and covers an area of one or more square meters. For reasons of space it has been found particularly useful for the light source to be disposed laterally, for example, in the region of a lateral edge, and for the emitted light to be coupled into the light-transparent, light-guiding planar element from the side. In the light-guiding planar element, the light travels primarily parallel to the light radiating surface. A deflector on the planar element ensures that the light coupled in is reflected and deflected toward the light radiating surface from which it then emerges. The deflector is designed such that deflection toward the light radiating surface takes place throughout the area of the light radiating surface, or if light is only to be emitted via part of the light radiating surface takes place at least in this area.

One possibility for implementing such a deflector takes the form of a patterning coating applied to one side of the planar element. The coating, which may be screen printed onto the glass or plastic planar element, creates a plurality of reflection centers, i.e. has micropatterning forming the reflection centers at the interface to the planar element. As an alternative to applying such a coating it is also conceivable to pattern the surface of the planar element itself, for example, to create the reflection centers in the surface, which is possible by mechanical, chemical, or physical surface treatment. The selective application or formation of the deflector, whether it be via the coating or the patterned surface itself, also makes it possible to define the region of the light radiating surface where light is actually to be radiated, or any shape of the light radiating surface itself, irrespective of the actual shape of the light-guiding planar element. Therefore, if, for example, because of corresponding installation requirements the light-guiding planar element must be made larger than the actual light radiating surface, this makes it possible for the deflector also to be applied or formed in the region where light is actually to be radiated. It is obviously also possible to implement corresponding radiation patterns by the deflector occupies a geometrical planar shape.

In order to improve the homogeneity of the radiated light, the planar element has, on the light radiating surface side, a diffuser or is assigned such a diffuser. The diffuser may be implemented as a planar, plate-like element which, like the light-guiding planar element, is of flat or curved design. Here, for example, it is conceivable to use a satinized glass or plastic plate which is placed over the glass or plastic planar element. The planar diffuser component also has a thickness of only a few millimeters, for example, 2-10 mm. A backplane which seals the lighting device to the rear is preferably disposed on the opposite side of the planar element.

In one embodiment, a plurality of light sources that couple light into the planar element are provided along the side. Particularly in the case of large-area planar elements and consequently long lateral edges and a large light radiating surface, it is thus possible for a plurality of edge light generating centers and light coupling points to be implemented. The lighting unit very narrow overall as a result of the lateral arrangement. The use and disposition of a plurality of lateral lighting elements offers the possibility of also being able to couple a large amount of light into the planar element. The lighting elements may be combined into a strip-like unit, which is laid along the lateral edge of the planar element where it is disposed in an appropriately fixed or encapsulated manner.

Although light sources in the form of incandescent or halogen lamps may be used, LEDs may also be used. LEDs are small and may be disposed without any problem in the region of thin lateral edges of the planar element, while at the same time providing a very high light yield. LEDs have a long useful life, and they generate little heat. A large number of LEDs may be incorporated in a very small space.

The light source or sources may be encapsulated in the installed state so that they are securely fixed. The light source (s) may be disposed on the lighting device in the region of the light radiating surface a non-transparent cover element which masks the light source(s) and which is at least large enough to ensure that it covers the light sources when viewed from the light radiating surface. This prevents a person from being able to look directly at an operationally sometimes very bright light source from the direction of the light radiating surface. For example, such a non-transparent cover element can even be visually attractive metal plate or rail which is disposed in the region of the lateral edge or which rotates. Plastic cover elements may also be used.

The lighting device includes a control device via which the brightness of the light source or sources, such as the LEDs, can be varied. The brightness and the amount of light radiated via the light radiating surface can be adapted or varied via the control device. when using a plurality of light sources, The control device can control and switch on the plurality of light sources either jointly or separately according to the requirements and situation when using a plurality of light sources. Whereas high brightness is required, for example, in order to position the patient or to connect or attach equipment or to perform surgical procedures, a reduced brightness is deemed to be sufficient, for example, during the examination, for example, the taking of images, which can consequently last from several minutes to hours. This can be directly controlled via the control device, for example, by the brightness being switchable between discrete brightness levels or steplessly dimmable between a maximum value and a minimum value via the control device. This enables the brightness to be varied as required, which also offers the possibility of creating a pleasant atmosphere conducive to enhanced patient comfort as and when required, particularly if the examination is a lengthy one.

In one embodiment, white light and light of at least one color can be emitted by the lighting device. If required, it is possible to switch from white to colored lighting via the control device. This makes it possible to communicate information to the examinee, for example, during image capture, the lighting changes from white to colored so that the examinee knows precisely when image capture commences. At the end of image capture, the lighting can be switched from colored to white again so that the end of image capture can be communicated. In this way it is also conceivable to indicate times during which the patient must not move, for example, or must hold his breath or must make particular movements if a particular type of imaging so requires, for example, in the field of magnetic resonance imaging. If the patient is to hold his breath, for example, this is indicated to him by switching to colored light which stays on until the breath-holding time has elapsed and the light can be switched back to white. This provides a very simple and intuitive way of communicating information. For example, switching to red light is conceivable, as people often associate red light with the communication of information In one embodiment, the bright white lighting is switched off and changed to a pleasant colored illumination which is invariably perceived as pleasant by the patient, thereby promoting his sense of well-being during the period of the examination. Colored light also sometimes has a therapeutic effect, sometimes assisting and promoting any healing processes, so that the advantages of color adjustability can be used in this respect also. Of course it is also possible here, depending on the arrangement of the light sources, to change steplessly from white light to colored light, for example, to dim down the white light and dim up the colored light, just as a clean switchover from white to colored light is also possible.

It is basically possible for white and colored light to be emitted in each case via the entire light radiating surface, for example, always using the entire light radiating surface for the different colored illuminations. Alternatively, white and colored light may be radiated in separate areas of the light radiating surface. When information is to be communicated via the lighting device, it is possible to implement, as it were, a kind of "information light" on the light radiating surface in a particular area via the colored lighting.

In one embodiment, dedicated light sources are assigned to the respective lighting colors. The lighting device incorporate a plurality of light sources and include at least one white light emitting light source and at least one colored light emitting light source, which can be controlled separately.

Alternatively, white light and any mixed colors of the radiated light may be produced by light mixing. For this purpose at least one red light, at least one blue light and at least one green light emitting light source can be provided which can be controlled separately. Depending on which light sources are activated and the intensity with which they are operated, white light or any other mixed color can be produced. LEDs are preferably used, for example, both white and colored LEDs. If the lighting device or the light-transparent planar element are sufficiently large, a large number of individual light sources or LEDs of each color can of course be employed, three LEDs of different colors being combined into groups in each case and disposed adjacently. The radiated light color may be continuously variable in order to ensure a gradual transition to any color.

Lighting of any desired color may be created to create particular atmospheres, even to the extent of allowing the examinee, particularly in the case of lengthy examinations, to select a desired color, for example, the color with which the examinee feels most at ease, to be radiated during the examination. Despite colored lighting, it is still possible for the person carrying out the examination to observe the patient, because the colored lighting always illuminates the examination area and/or its periphery. Continuous color changing is possible here, for example, in order to promote patient comfort during long examinations. A color change may take place continuously, the lighting constantly changing from one color to another. Such a light display is experienced as pleasant and relaxing by the patient.

The emission of color basically enables information to be conveyed to the patient being examined. In order to increase the depth of information, at least one display serving to represent information and/or images may be disposed on or in the lighting device. The display may be assigned to the lighting device. It is basically possible to incorporate a corresponding display in a designated area of the lighting device, for which purpose there is provided an appropriate cutout in the planar element and the diffuser placed in front of or in the backplane in which such a display is integrated. Any information can be displayed to the patient, such as how long the examination has already been in progress or still has to run, any instructions for him to hold his breath or information for the person performing the examination, for example, concerning the compressive force exerted on the breast, the compression density, the capture angle or general patient data in the case of a mammography unit. Alternatively, or in addition to, such a display it is also possible to provide at least one projection device by which items of information and/or images can be projected onto an area of the light radiating surface of the lighting device. A separate projection unit is used which beams information/images onto the lighting device.

The generation of colored light makes it possible not only to convey information or create a pleasant examination atmosphere but also, by color changes, to give visual stimuli of the kind sometimes required, for example, in the context of functional imaging, such as in magnetic resonance or computed tomography scans. For example, if the light is switched from white to bright red, certain activities are stimulated in the brain which can be detected via functional imaging. By showing any information on a display or by a projection device it is also possible to selectively give other optical stimuli which stimulate other brain centers, for example, during reading or the like.

The examination device can be an x-ray device, for example, one used to examine a standing examinee, in which case the lighting device is disposed in a vertically upright manner. The equipment may be a mammography unit, for example, wherein the lighting device is disposed behind the x-ray imaging device disposed in a vertically displaceable manner on a vertical column. A mammography unit may include an x-ray tube and the detector, such as a digital flat-panel detector. The tube and detector can be moved up and down a vertical column at a fixed distance from one another via a suitable mechanism. The lighting device is now disposed in front of the vertical column, virtually covering it from the front. Depending on design, the lighting device, here a flat plate, faces out at the side of or above the x-ray imaging means, so that the space in front of the lighting device, the periphery of the examination area, and the examination area between x-ray tube and detector can be partially or completely illuminated. The patient stands in front of the x-ray imaging device and in front of the lighting device, for example, looks in the direction of the illuminated lighting device. The person performing the examination can approach the x-ray imaging device from the side, for example, can have an optimum view of the examination area and position the patient as well as operate the compression unit via which the breast is compressed. The relevant area or areas are optimally illuminated via the planar lighting device, the patient also being offered a pleasantly lit environment, especially if during the examination the brightness is reduced or the lighting is changed to another color.

The tubes and detector can be moved jointly to capture vertical radiographic images, with other x-ray machines horizontal imaging is possible. The detector is often mounted in a vertically displaceable manner to a vertical column in order to be able to position it in different positions relative to the patient standing in front of same. The x-ray tube is on a floor or ceiling support and can be moved independently of the detector. Such devices can be used, for example, for chest x-rays. Incorporating a planar lighting device is now possible also for equipment of this kind. The planar lighting device is disposed behind the detector and in front of the vertical column, for example, covering the vertical column and radiating frontward directly into the examination area or periphery thereof.

Disposing the lighting device between column and movable image recording section lends itself to all cases in which part of the x-ray imaging device or the entire x-ray imaging device is movably mounted to a column. For this purpose the lighting device is advantageously U-shaped, wherein a support arm carrying the x-ray imaging device or the detector and guided on the vertical column extends between the legs of the U. The lighting device may be a one-part component which encloses the x-ray apparatus as a kind of frame and is penetrated by the support arm which links the imaging device/detector to the vertical column. This ensures a very large light radiating surface while at the same time allowing the integration of the lighting device which can also be retro-fitted to existing equipment.

The x-ray imaging device may be disposed on a support which is disposed on a trolley movably guided on ceiling-mounted guide, and that a positioning table is provided for the examinee, wherein the lighting device is disposed on the trolley. This is a ceiling-guided unit, for example, having a C-arm on which the x-ray tube and the detector are disposed, or two separate supports disposed on the guide trolley, one supporting the tube and the other the detector. The lighting device is disposed on the trolley, which is generally relatively large-area to allow x-y guiding on the ceiling-mounted guide. The shape of the lighting device depends on the shape of the trolley and may be, for example, square, circular, or rectangular, depending on the design of the trolley. It is also possible to use a large-area lighting device here which radiates from above directly onto the examination area, in this case the patient positioning table.

The examination device may be a magnetic resonance device or a computed tomography device. Both have at least one essentially cylindrical tunnel to accommodate the examinee. The lighting device lines the tunnel at least over part of its length and at least over part of its circumference. The lighting device is incorporated inside the tunnel, mainly in the region of the edge of the tunnel bore and at the side on which the patient positioning table is introduced. In this region the integration of the lighting device is uncritical inasmuch as the imaging magnetic fields are generated more in the center of the tunnel. The entire tunnel can be termed the examination area and the tunnel entrance the periphery of the examination area in which the homogeneous planar illumination is possible using the lighting device. The lighting device is curved here because of the cylindrical shape of the tunnel and can extend over a length of, for example, 30 or 40 cm inside the tunnel and, for example, through 180° when disposed centrally on the upper cylinder wall, or even around the circumference. It is generally located in the region of the head of the patient who can then be given color information or the like, combined with optimum illumination of this area for the person carrying out the examination. An appropriate color atmosphere can also be created or brightness adjustments made depending on the design of the lighting device and requirements.

Alternatively, or additionally to, the lighting device may be disposed in a tunnel, when the equipment has a cylindrical tunnel. The lighting device is disposed on the outside of the equipment, such as the end face, from which side the patient positioning table is introduced into the tunnel. The lighting device occupies at least part of the essentially annular end face adjacent to the tunnel. Via said lighting device, the peripheral region in front of the tunnel, for example, in front of the examination device itself, is illuminated. The lighting device can be implemented, for example, as a half ring and only run round the upper half, or extend further round. The lighting device enables the area in front of the tunnel to be illuminated with the table retracted, so that the person performing the examination can have an optimum, evenly illuminated peripheral area for placing the patient on the table and attaching any local coils.

Instead of a cylindrical tunnel with cylindrical magnets, a variant of a magnetic resonance device provides magnets disposed horizontally one above the other and spaced apart with the examination area located therebetween. The lighting device is disposed on the upper magnet and at least partially occupies the upper magnet. In the open system, the patient can be introduced from the front or from the side between the magnets. If an action is to be performed on the patient, the examinee is accessible between the two magnets. The lighting device is disposed on the upper magnet or the upper magnet's paneling, and therefore radiates downward. For example, it can be disposed on the edge region of the magnet as a circumferential ring or half-ring.

DETAILED DESCRIPTION

Figure 1:
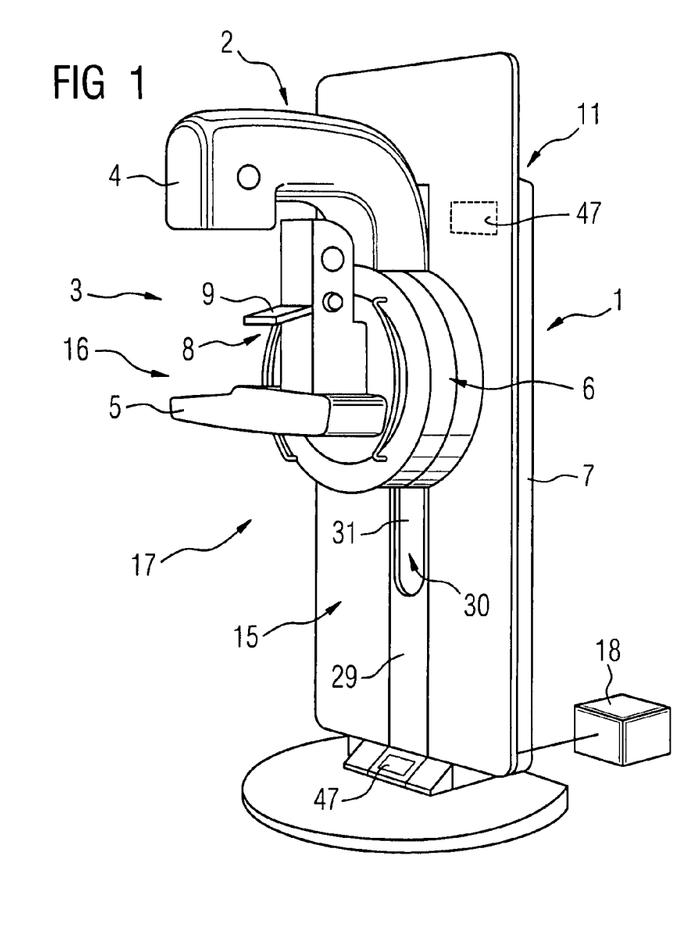
FIG. 1 shows a schematic diagram of an examination device in the form of a mammography unit with lighting device.

FIG. 1 shows an examination device 1 in the form of an x-ray mammography unit 2 including an x-ray imaging device 3 with an x-ray source disposed in an upper arm 4 and a detector disposed in a lower support 5. The x-ray imaging device 3 is disposed on a displacement device 6 allowing vertical movement along a vertical column 7, such that the vertical position of the x-ray imaging device 3 may be adapted to the patient's height. A compression device 8 is vertically movable with the x-ray imaging device 3. The compression device 8 is used to compress the breast by the vertically displaceable compression plate 9.

Movement is provided via a suitable motor system disposed in the region of the vertical column 7 on which the displacement device 6 is guided in a vertically movable manner.

Figure 3:
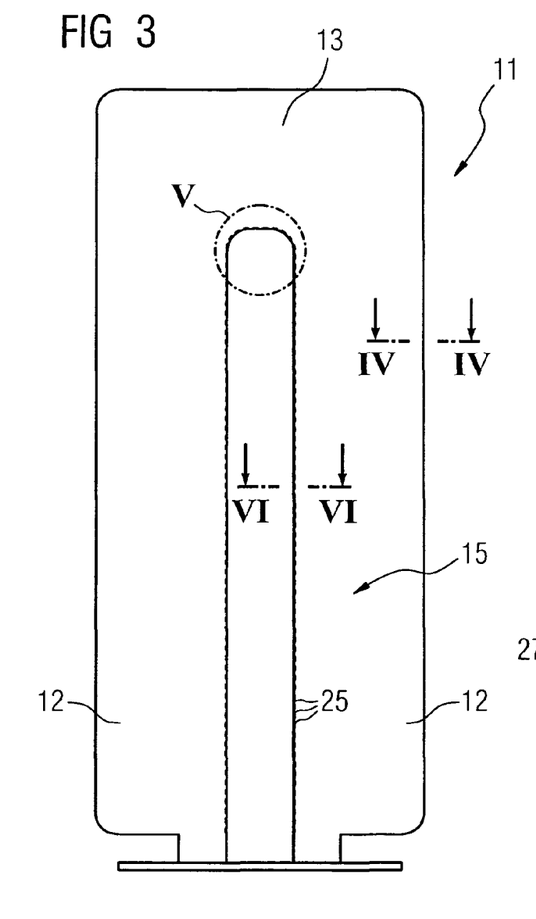
FIG. 3 is a front view of the lighting device from FIG. 1.
Figure 4:
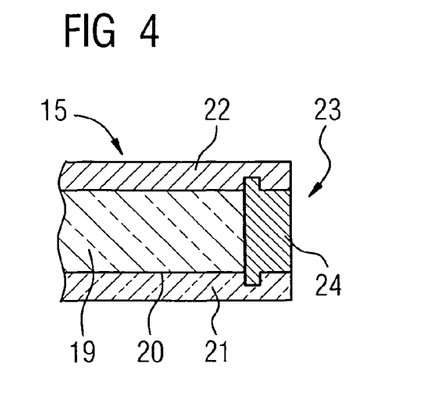
FIG. 4 shows a partial cross-sectional view in the direction marked IV-IV in FIG. 3.

Between the vertical column 7 or rather its outer paneling 10 and the x-ray imaging device 3, the circularly housed displacement device 6 is incorporated, as shown in FIG. 1. A planar lighting device 11 which, as shown in FIG. 3, is essentially U-shaped with two lateral members 12 and a cross member 13. The two lateral members 12 are penetrated by a support arm, which is part of the displacement device 6 and via which linkage is provided to the displacement mechanism of the vertical column 7. The lighting device 11 is plate-like and slim, so that it can be easily incorporated in the space between the vertical column paneling 10 and the displacement device 6 or the housing 14. For example, the vertical column paneling 10 can be set to increase the size of the gap between the paneling 10 and the paneling 14 of the displacement device 6. The plate-like, large-area lighting device 11 is fixed via suitable fixing accessories, such as connecting screws or quick-release fastenings using toggle joints to corresponding fixing accessories on the vertical column paneling 10.

The lighting device 11 has a light radiating surface 15 via which light can be emitted forward in the direction of the examination area 16, which is here located between the x-ray tube and the radiation detector, and of the peripheral area 17, such as the area to the side of examination area. In the example shown, the light radiating surface 15 corresponds to the entire front surface of the lighting device 11, via which light can be emitted in a large-area and essentially homogeneous manner. Even if, as shown in FIG. 1, parts of the light radiating surface 15 are obscured by the x-ray imaging device 3 or the displacement device 6, the extensive size of the light radiating surface 15 permits sufficiently large surface areas, which are unobscured, to emit a sufficient amount of light into the examination area 16 and/or the peripheral area 17. As shown in FIG. 1, operation of the lighting device 11 may be, for example, controlled via an appropriate control device 18, which controls the plurality of light sources. The control device 18 can be the central controller of the mammography unit 2 (in the case of the other example, of the relevant examination equipment).

FIGS. 3-6 show the lighting device 11. The lighting device 11 includes three planar components, such as a first light-transparent and light-guiding planar element 19, which can be made of glass or transparent plastic, such as PMMA or PC. To the rear side 20, there is either applied a coating by which light reflection or light scatter centers are implemented in order to reflect light coupled in from the side in a homogeneous manner toward the light radiating surface 15. At the back, a backpanel 21 closes off the lighting device 11 to the rear, for example, to the side of the vertical column 7. On the opposite side is another planar element in the form of a diffuser 22, which can be, for example, a satinized glass plate or a satinized plastic plate. The diffuser 22 is the front closure and the front light radiating surface 15. Disposed in the region of the outer edge 23 is an edge closure component 24, which in the example shown has a T-shaped cross-section and is inserted in corresponding grooves implemented along the boundary edge on the backpanel 21 and diffuser 22. The edge closure component 24 is not transparent, and can even be made reflecting on its inward facing side (e.g. polished or provided with a coating) in order to reflect light back again into the planar element 19.

Figure 6:
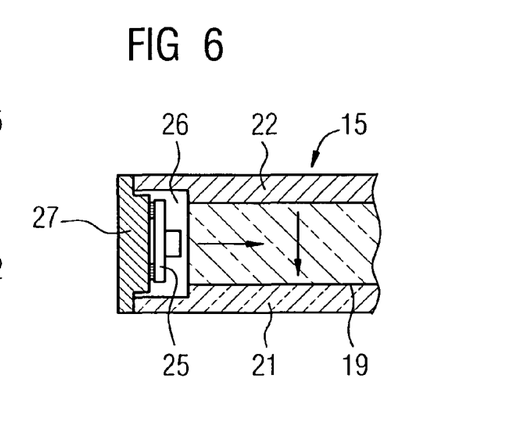
FIG. 6 shows a partial cross-sectional view in the direction marked VI-VI in FIG. 3.

The light radiated via the light radiating surface 15 is coupled via a plurality of individual light sources 25 from the inner lateral edge of the lighting device 11 or the light-transparent light-guiding planar element 19 into the planar element 19. As FIG. 6 shows, the backpanel 21 and the diffuser 22 are recessed in the region of the inner edges so as to form a mounting space 26 in which the light sources 25, such as a plurality of LEDs combined into a strip-shaped unit, are accommodated. The light sources 25 are bonded onto an inner edge closure component 27, which is bonded to the backpanel 21 and the diffuser 22 or fastened thereto in some other manner. As indicated by the arrow in FIG. 6, the light is coupled in virtually parallel to the light radiating surface 15. As indicated by the second arrow in FIG. 6, the light is reflected via the plurality of evenly distributed reflection centers implemented on the back side 20 toward the light radiating surface 15 via which it can then emerge.

Because of the light-conducting or light-guiding properties of the planar element 19 and of the arrangement of the plurality of light sources 25 over the entire length of the inner edge of the planar element 19, the light is distributed throughout the planar element 19. Reflections in the direction of the light radiating surface 15 take place over the entire surface of the rear side 20 if the latter is provided in its entirely with reflection centers in the form of the coating or by direct patterning of the rear side 20. The lighting device may emit homogeneous light such as light with a uniform brightness distribution, over the entire light radiating surface 15, consequently enabling it to illuminate the examination area 16 and the peripheral area 17, uniformly with homogeneous light.

Figure 5:
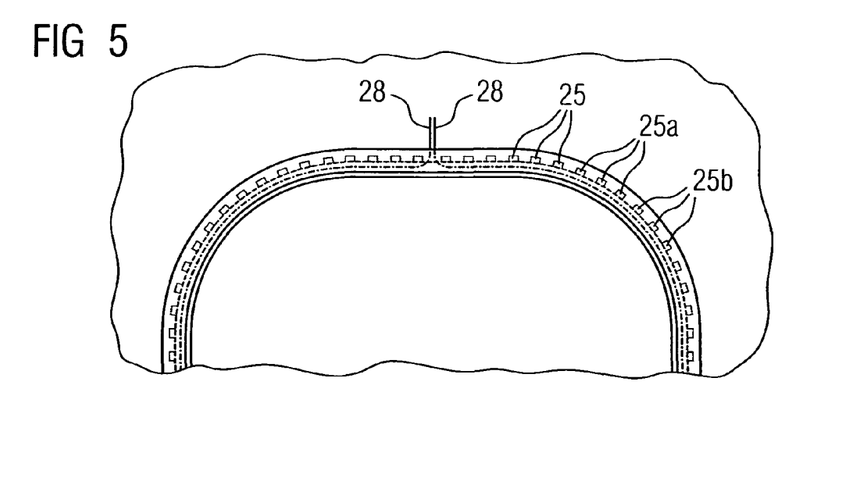
FIG. 5 shows an enlarged partial view of region V in FIG. 3.

As shown in FIG. 5, the individual light sources 25 are all disposed next to one another in a row. As FIG. 5 shows, in the upper region of the recess between the two lateral members 12 the connecting wires 28 of the two light source strings, which extend to the right and left, are brought out and routed to the control device 18 or to a power source. As already described, the light sources 25 may all be white light emitting light sources, such as LEDs. Only white light would be able to be radiated via the lighting device 11. The emitted brightness can be adjusted via the control device 18. For example, the brightness can be set to maximum at the start of an examination, when the patient has to be positioned, or when, for example, a biopsy has to be taken. When actual image capture then commences, the brightness can be reduced somewhat, which is conducive to patient comfort.

As an alternative to using only white light emitting light sources 25, either alternately or only in particular areas, light sources 25 may emit colored light. For example, every second LED can be a red emitting LED, or a number of red emitting LEDs can be provided in a designated longitudinal section on both sides of the inner lighting device edge, the colored light emitting LEDs or light sources may be separately controllable via the control device 18. This makes it possible, if required, to switch either completely or in areas, depending on how the colored LEDs are arranged, from white lighting to colored lighting, or produce both together. This offers the possibility of providing the patient with information via the color of the light, for example, indicating that imaging has commenced. Combined with information inferable from the lights, the patient should stand completely still, and also that imaging is complete when the colored lighting is turned off. It is also conceivable for the colored lighting to be able to be varied in its brightness as required via the control device 18 or to switch white and colored light in corresponding brightness levels, or to dim both up and down in opposite directions if a complete, full-area color change is to take place.

In one embodiment, light sources, which emit light of different colors, may be used. Accordingly, light mixing on the light radiating surface 15 of a desired color of light may be emitted. For example, three adjacently disposed light sources 25, such as LEDs, can be combined into groups each comprising a red, a green and a blue emitting LED, as illustrated by the two groups of three 25a and 25b. Each individual LED within such a group of three is separately controllable via the control device 18. All the LEDs of the same color, which are disposed in a distributed manner on the lateral edge, may be jointly, simultaneously controllable. By skillful light mixing it is possible to produce on the one hand white light, and on the other any required mixed color. This offers the possibility of being able to radiate homogeneous light via the entire radiating surface 15 both in respect of brightness or intensity and of the color of the light. For example, at the start of the examination, when the patient enters the mammography unit 2 and has to be positioned, white light is generated and radiated. When positioning is complete, it is then possible to switch to a light color e.g. desired by the patient, which is then emitted via the light radiating surface 15. The control device 18 then controls the corresponding LEDs in the manner required for generating the desired color of light. This enables a pleasant atmosphere to be created for the patient in connection with such an examination which is often experienced as unpleasant. The light mixing enables appropriate information to be conveyed, even if the light color has previously been changed from white light to a desired color. For it is readily possible, at the start of actual imaging, particularly when a plurality of separate images are to be taken consecutively from different positions, to switch for example to red light in order to signal to the patient that imaging is in progress, and to switch back to the desired light color when imaging is complete. Any color variations and control sequences are conceivable.

As an alternative to the illustrated arrangement of the light sources 25 on the inner lateral edge of the lighting device 11, a light-proof component, for example, an internally reflecting closure in the form of an edge closure component, may be disposed externally and disposed internally (e.g., on the inside) The shape of the lighting device is not limited to a rectangular shape. The shape of the lighting device may be oval in order to implement, toward the side, a larger radiating surface region in the area in which the displacement device 6 is moved in front of the light radiating surface 15.

As FIG. 1 also shows, there is provided between the two lateral members 12 of the lighting device 11 a cover element 29, which has a central gap 30 in which a blind 31 is disposed. The blind 31 closes the space to the vertical column. The cover element 29 may, on the front side, such as the light radiating surface 15, cover the light sources 25 so that it is not possible to look directly into same from the front or from the side. The boundary area of the cover element 29 may overlap the light radiating surface 15 in the boundary edge region in which the light source strips run.

Figure 2:
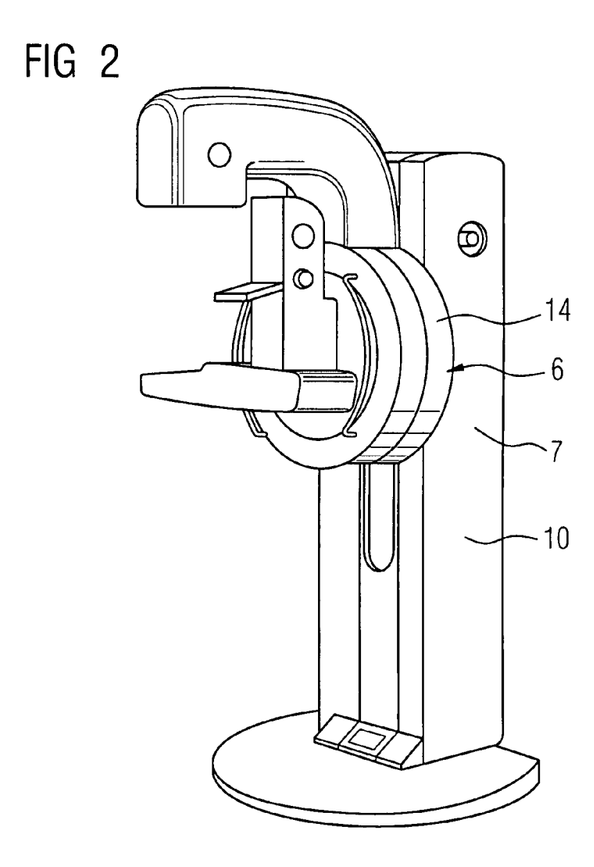
FIG. 2 shows the mammography unit from FIG. 1 without lighting device.

At the base of the examination device there is also provided a display 47, which can show information for the doctor providing treatment. A display 47, for example, a slim LCD display, can additionally or alternatively be provided on the lighting device 11, as indicated by the dashed lines in FIG. 2. The diffuser 22 is provided with a recess in which the display is inserted, any wire connections can be routed backward via an opening in the planar element 19 and the backpanel 21. The display 47 may be mounted directly on the diffuser 22, so that the lighting device remains basically unchanged in its design. When the display is disposed in this position, relevant information for the patient can be displayed on the display 47. The incorporation of the display 47 is possible for all the lighting devices of the exemplary embodiments described below.

Instead of a display 47, an area can also be used as a projection surface, for example, for a projection device such as a beamer located on the arm 4, by which information can be projected onto the projection surface. This is in some circumstances also possible while the lighting device 11 is operating, if the light output of the projection device is large enough. It is also possible to use the projection device and a projection surface with the embodiments described below.

Further examples of different types of examination devices, which have at least one lighting device 11 of basically the same design as that shown in FIGS. 1-6, will now be described with reference to FIGS. 7-9, so that in this respect and in respect of the operating principle. Where possible the same reference characters are used for the same elements.

Figure 7:
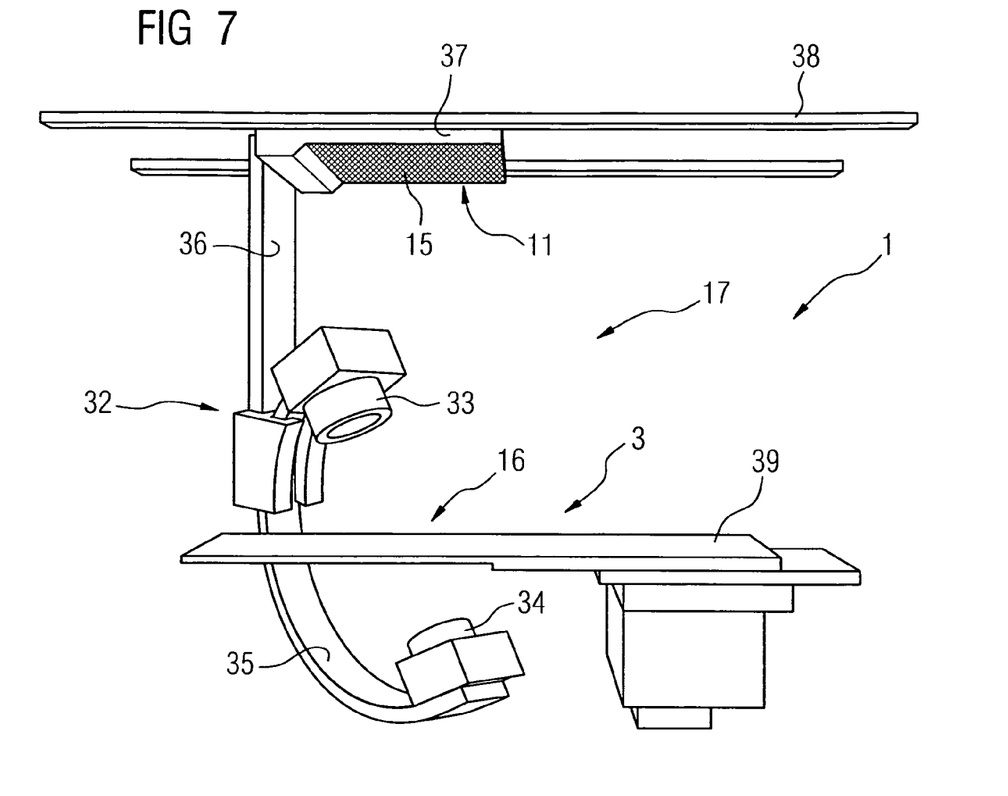
FIG. 7 shows a schematic diagram of another type of examination device in the form of a C-arm x-ray device.

FIG. 7 shows another examination device 1. The examination device 1 is in the form of a C-arm x-ray machine 32. The examination device 1 includes an imaging device 3 having an x-ray tube 33 and a detector 34, both of which are disposed on a C-arm 35, which is in turn mounted to a support 36 that is disposed on a trolley 37 that can be moved in the x-and possibly y-direction on ceiling-mounted guide 38. The examination device 1 may include a positioning table 39 for a patient to be examined. The examination area 16 is located between x-ray tube 33 and detector 34, the peripheral area 17 primarily above the patient positioning table 39, for example, where the patient is located.

A lighting device 11 may be disposed on the underside of the trolley 37. The lighting device 11 may be a large-area lighting device. The lighting device 11 may have a rectangular shape, which corresponds to the basic shape of the trolley 37, but can have any other shape required and even overlap the basic trolley shape at the side. The light via the light radiating surface 15 is here reflected downward, as the examination area 16 and the peripheral area 17 are located under the light radiating surface 15. Because of the design of the lighting device 11, the emitted light is homogeneous over the entire light radiating surface 15 and, when using appropriate light sources 25, both white and colored light can be radiated. In this connection reference should be made to the previous descriptions.

The examination area 16 and the peripheral area 17 may be illuminated with white light, for example, at the start of the examination when the patient has to be placed on the patient positioning table 39 and positioned on the positioning table 39 in relation to the imaging device 3 so that the person performing the examination has an optimally and brightly lit working environment. At the start of x-raying, the brightness can be reduced or the light switched to colored. If necessary, to the lighting may be used to convey information via the color of the light. The patient, who is often arranged facing the lighting device 11, is immediately aware of any color change, so that it can be indicated, for example, that the patient should not move any more from the color change onwards. Where desired and necessary, a lighting atmosphere appropriately conductive to patient comfort can be created via the corresponding lighting color, such as during lengthy x-ray sessions.

Figure 8:
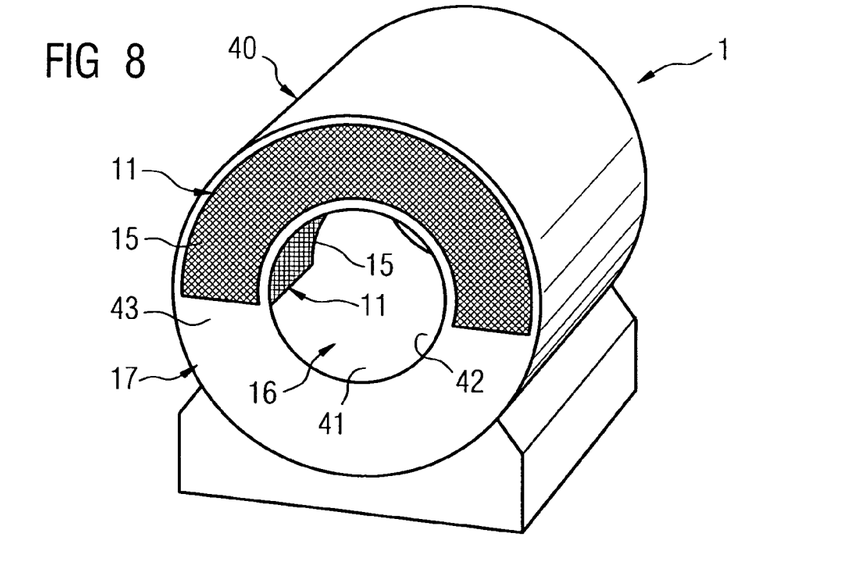
FIG. 8 shows a schematic diagram of an examination device in the form of a magnetic resonance or computed tomography device.

FIG. 8 shows another embodiment of an examination device 1. The examination device 1 is in the form of an MRI scanner 40, or a CT (computed tomography) unit. Irrespective of the specific type of equipment, the examination device 1 here has a cylindrical tunnel 41 into which the patient is introduced by a patient positioning table, which is positioned outside the tunnel 41 for accommodating the patient. The examination area 16 is inside the tunnel 41, for example, in the center. The peripheral area 17 is outside the tunnel 41, but also possibly extending some distance into the tunnel 41.

A lighting device 11 is disposed inside the tunnel 41, for example, at the front edge. The lighting device 11 extends a certain length into the tunnel 41, but only so far as not to affect imaging, which in the case of an MRI scanner takes place using suitable magnetic fields. The lighting device 11 is, for example, mounted to or locally replaces the internal paneling 42 of the upper region of the tunnel. Because of the cylindrical shape of the tunnel 41, it is curved and extends through more than 180° in the example shown. The light radiating surface 15 is directed downward, for example, toward the patient, who is moved under the lighting device 11 or positioned there or in its illuminated region.

The lighting device 11 may homogeneously illuminate part of the examination area 16 and/or its peripheral area 17 located in front of the examination area 16. The curved lighting device 11 corresponds to the design described in the introduction. The light sources are preferably disposed on the front or back long end-edge.

The patient's head, if it is not the specific object of the examination, is located in the patient receiving area, he can be given light-optical information. It is possible, before and during the examination, to provide optimum area lighting for the person performing the examination and create a pleasant lighting atmosphere.

This is possible in the case of the examination device 1 from FIG. 8 via a second lighting device 11 which is provided on the end face 43 of the MRI scanner 40 or CT machine. The additional or alternative lighting device 11 is here of U-shaped design and extends in the example shown through approximately 180° around the tunnel 41. It too offers the possibility of large-area radiation of light via the light radiating surface 15. Once again, similarly to the lighting device 11 from FIG. 1, the light sources can be in the region of the inner edge, although it is equally conceivable for them to be disposed outside. The light sources can be any kind of white or colored light emitting elements. Again reference should be made to the earlier descriptions. The lighting device 11 radiates forward into the peripheral region 17 in front of the examination device 1, for example, where the retracted patient positioning table is located to receive the patient. This makes it possible for this area to be optimally illuminated in order to enable appropriate preparatory actions to be carried out on the patient, such as arranging local coils.

Figure 9:
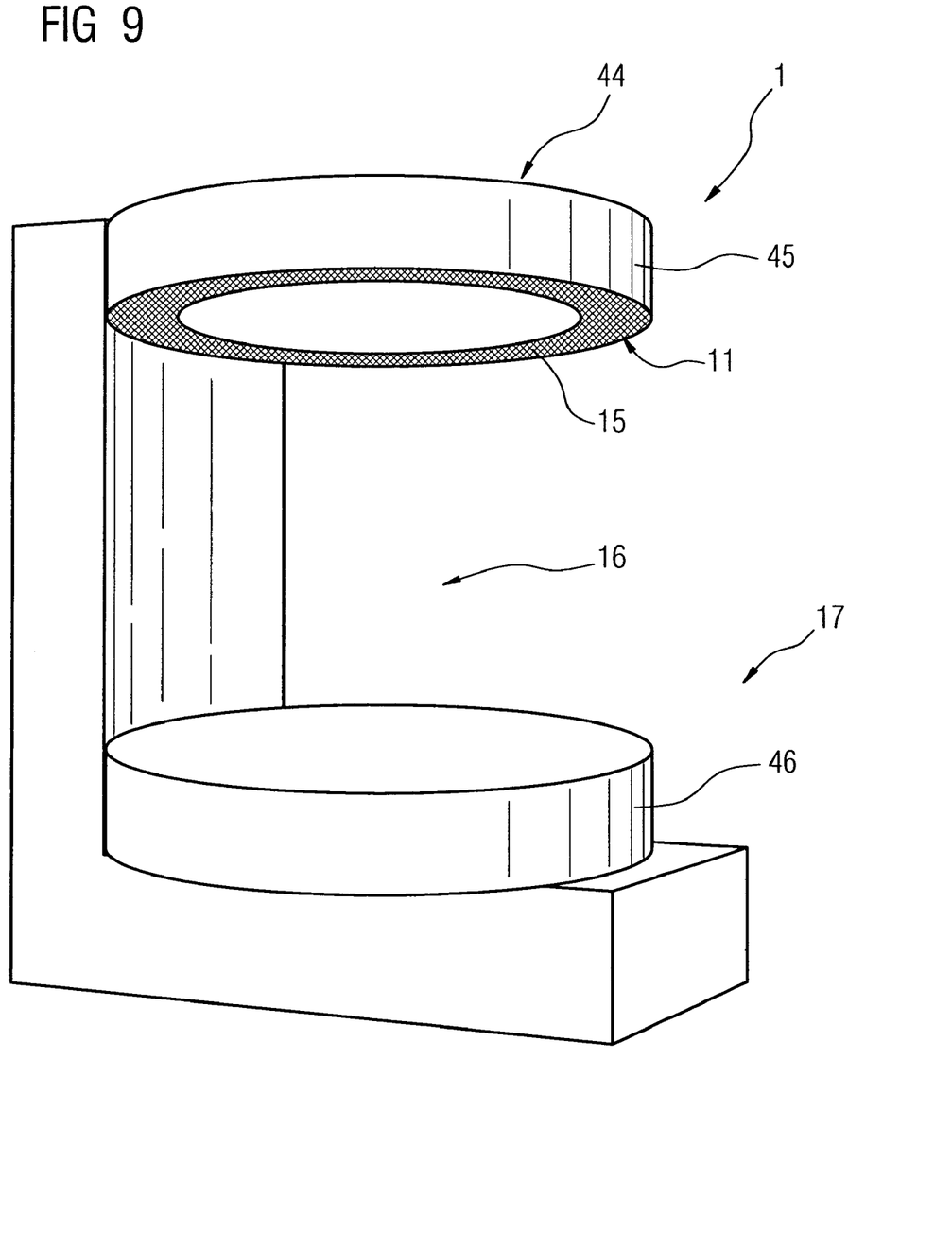
FIG. 9 shows a schematic diagram of an examination device in the form of another type of magnetic resonance device.

FIG. 9 shows another examination device 1. The examination device 1 is an MRI scanner 44 having two separate magnets 45, 46 disposed horizontally one above the other, between which the examination area 16 and outside of which the area 17 peripheral thereto is located. Disposed on the upper magnet 45 is a lighting device 11 which is in this case annular and runs around the edge of the magnet 45. The light radiating surface is again directed downward toward the examination area 16 so that it can also be optimally and homogeneously illuminated. The design of the lighting device 11 corresponds to the design already described, and here too the light sources can preferably be disposed on the inner lateral edge. They can again be white or colored light emitting LEDs.

Each lighting device 11, regardless of where it is now disposed, is attached via suitable fastening devices such as screws, quick-release fasteners in the form of toggle joints, bayonet mounts. For this purpose there can be disposed on the backpanel 21 of each lighting device 11 appropriate fixing devices in the form of retaining rails or retaining brackets, which is connected to corresponding fixing device on the respective component of the examination device. Such a component can be, for example, a paneling section on which the lighting device 11 is mounted, or a frame construction, for example, of the trolley 37. The type and positioning of the fixing device on the lighting device side obviously depends on the fixing possibility on the corresponding component of the examination device.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical examination apparatus comprising:
   an examination area, in which an examinee is examined using an imaging device; and
   at least one planar lighting device that emits homogeneous light via a light radiating surface, the at least one planar lighting device including at least one light source, by which at least part of the examination area, an area peripheral to the examination area, or the at least part of the examination area and the area peripheral to the examination area are illuminatable,
   wherein a display configured for showing information, images, or the information and the images is disposed on or in the at least one planar lighting device, or a projection device is configured to project the information, the images, or the information and the images onto an area of the light radiating surface of the at least one planar lighting device.

2. The medical examination apparatus as claimed in claim 1, wherein the at least one planar lighting device is plate-like and of flat or curved design and at least partially delimits the examination area or the area peripheral to the examination area.

3. The medical examination apparatus as claimed in claim 1, wherein the at least one planar lighting device comprises a light-guiding planar element, the light-guiding planar element having a deflector that deflects light coupled in laterally via the at least one light source to the light radiating surface.

4. The medical examination apparatus as claimed in claim 3, wherein the deflector is a coating applied to one side of the light-guiding planar element or a patterning of a surface of the light-guiding planar element.

5. The medical examination apparatus as claimed in claim 3, wherein the light-guiding planar element has a diffuser provided on a side of the light radiating surface or a diffuser that is assigned to the side of the light radiating surface.

6. The medical examination apparatus as claimed in claim 3, wherein the at least one light source comprises a plurality of light sources for coupling light into the light-guiding planar element, the plurality of light sources being provided along a side.

7. The medical examination apparatus as claimed in claim 6, wherein the plurality of light sources are combined in a strip-like unit.

8. The medical examination apparatus as claimed in claim 6, wherein the plurality of light sources are LEDs.

9. The medical examination apparatus as claimed in claim 1, wherein the at least one light source comprises a plurality of light sources, and
   wherein in a region of the light radiating surface, the at least one planar lighting device is assigned a non-transparent cover element masking the plurality of light sources.

10. The medical examination apparatus as claimed in claim 1, wherein the at least one light source comprises a plurality of light sources, and
    wherein the at least one planar lighting device incorporates a control device via which the brightness of the plurality of light sources is operable to be varied.

11. The medical examination apparatus as claimed in claim 10, wherein via the control device, the brightness is operable to be switched between discrete brightness levels, or the brightness is operable to be continuously dimmed between a maximum value and a minimum value.

12. The medical examination apparatus as claimed in claim 1, wherein white light and light of at least one color are operable to be emitted by the at least one planar lighting device.

13. The medical examination apparatus as claimed in claim 12, wherein the white light and the light of at least one color are operable to be radiated in separate regions of the light radiating surface, or the white light or the light of at least one color is operable to be radiated via the entire light radiating surface.

14. The medical examination apparatus as claimed in claim 12, wherein the at least one light source comprises a plurality of light sources that incorporates at least one white light emitting light source and at least one separately controllable colored light emitting light source.

15. The medical examination apparatus as claimed in claim 12, wherein the at least one light source comprises at least one red light emitting light source, at least one blue light emitting light source, and at least one green light emitting light source that are separately controllable.

16. The medical examination apparatus as claimed in claim 15, wherein a radiated light color is continuously variable.

17. The medical examination apparatus as claimed in claim 1, further comprising an x-ray device.

18. The medical examination apparatus as claimed in claim 17, further comprising an examination device for examining a standing examinee, the at least one planar lighting device being disposed in a vertically upright manner.

19. The medical examination apparatus as claimed in claim 18, further comprising a mammography unit,
wherein the at least one planar lighting device is disposed behind the x-ray device, which is disposed in a vertically movable manner on a vertical column.

20. The medical examination apparatus as claimed in claim 17, wherein the x-ray device comprises an x-ray machine with a detector disposed vertically and in a vertically movable manner on a vertical column, and
wherein the at least one planar lighting device is disposed behind the detector.

21. A medical examination apparatus comprising:
an x-ray imaging device and a detector;
an examination area, in which an examinee is examined using the x-ray imaging device; and
at least one planar lighting device that emits homogeneous light via a light radiating surface, the at least one planar lighting device including at least one light source, by which at least part of the examination area, an area peripheral to the examination area, or the at least part of the examination area and the area peripheral to the examination area are illuminatable,
wherein the at least one planar lighting device is disposed the x-ray imaging device, the x-ray imaging device being disposed in a movable manner on a vertical column,
wherein the at least one planar lighting device has a U-shape and is disposed between the vertical column and the x-ray imaging device or the detector, and
wherein a support arm supporting the x-ray imaging device or the detector and guided on the vertical column extends between two extensions of the at least one U-shaped planar lighting device.

22. The medical examination apparatus as claimed in claim 17, wherein the x-ray device is disposed on a support that is disposed on a trolley movably guided on a ceiling-mounted guide, and a positioning table is provided for the examinee, and
wherein the at least one planar lighting device is disposed on the trolley.

23. The medical examination apparatus as claimed in claim 1, further comprising a magnetic resonance imaging (MRI) scanner or a computed tomography (CT) device.

24. The medical examination apparatus as claimed in claim 23, further comprising an essentially cylindrical tunnel for the examinee,
wherein the at least one planar lighting device lines the essentially cylindrical tunnel over at least part of a tunnel length and over at least part of a tunnel circumference.

25. The medical examination apparatus as claimed in claim 23, further comprising an essentially cylindrical tunnel for the examinee,
wherein the at least one planar lighting device occupies at least part of an essentially annular end face of the medical examination apparatus adjacent to the essentially cylindrical tunnel.

26. The medical examination apparatus as claimed in claim 23, wherein the MRI scanner has two magnets disposed horizontally and spaced apart from one another,
wherein the examination area is located between the two magnets, and
wherein the at least one planar lighting device is disposed on and partially occupying an upper magnet of the two magnets.

* * * * *

UNITED STATES PATENT AND TRADEMARK OFFICE
CERTIFICATE OF CORRECTION

| | |
|---|---|
| PATENT NO. | : 8,083,389 B2 |
| APPLICATION NO. | : 12/232481 |
| DATED | : December 27, 2011 |
| INVENTOR(S) | : Gerhard Helmreich, Martin Ramsauer and Michael Richenberger |

It is certified that error appears in the above-identified patent and that said Letters Patent is hereby corrected as shown below:

In the claims:
Column 14, claim 10, line 49, replace "the brightness" with "a brightness"
Column 15, claim 21, line 38, add "behind" after "disposed"

Signed and Sealed this
Fifteenth Day of March, 2016

Michelle K. Lee
*Director of the United States Patent and Trademark Office*